(12) United States Patent
Arambula et al.

(10) Patent No.: US 8,343,163 B1
(45) Date of Patent: Jan. 1, 2013

(54) SPINAL IMPLANT INSTALLATION DEVICE

(75) Inventors: Jared Arambula, San Diego, CA (US); Benjamin VerHage, San Diego, CA (US); Nathan Lovell, Encinitas, CA (US)

(73) Assignee: NuVasive, Inc., San Diego, CA (US)

( * ) Notice: Subject to any disclaimer, the term of this patent is extended or adjusted under 35 U.S.C. 154(b) by 411 days.

(21) Appl. No.: 12/378,685

(22) Filed: Feb. 17, 2009

Related U.S. Application Data

(60) Provisional application No. 61/028,886, filed on Feb. 14, 2008, provisional application No. 61/105,384, filed on Oct. 14, 2008.

(51) Int. Cl.
*A61B 17/58* (2006.01)

(52) U.S. Cl. ........................................................ 606/99

(58) Field of Classification Search ................ 606/86 A, 606/90, 99, 246–249; 623/17.11–17.16
See application file for complete search history.

(56) References Cited

U.S. PATENT DOCUMENTS

| | | | |
|---|---|---|---|
| 3,486,505 A | 12/1969 | Morrison | |
| 5,063,979 A * | 11/1991 | Johnson | 144/48.6 |
| 5,431,658 A | 7/1995 | Moskovich | |
| 5,860,973 A | 1/1999 | Michelson | |
| 6,159,215 A | 12/2000 | Urbahns | |
| 6,478,800 B1 * | 11/2002 | Fraser et al. | 606/99 |
| 6,652,533 B2 | 11/2003 | O'Neil | |
| 6,755,841 B2 | 6/2004 | Fraser | |
| 7,118,580 B1 | 10/2006 | Beyersdorff | |
| 7,169,182 B2 | 1/2007 | Errico | |
| 7,320,689 B2 | 1/2008 | Keller | |
| 7,404,795 B2 | 7/2008 | Ralph | |
| 7,918,891 B1 | 4/2011 | Curran | |
| 2004/0225295 A1 | 11/2004 | Zubok | |
| 2005/0165408 A1* | 7/2005 | Puno et al. | 606/99 |
| 2006/0241641 A1 | 10/2006 | Albans | |
| 2007/0162040 A1 | 7/2007 | Grabowski | |
| 2008/0132902 A1 | 6/2008 | Bertagnoli | |
| 2008/0154301 A1 | 6/2008 | de Villiers | |
| 2008/0161817 A1* | 7/2008 | Parsons et al. | 606/90 |
| 2008/0177275 A1* | 7/2008 | Wing et al. | 606/99 |
| 2008/0269764 A1 | 10/2008 | Blain | |

* cited by examiner

*Primary Examiner* — Kevin T Truong
*Assistant Examiner* — Diana S Jones
(74) *Attorney, Agent, or Firm* — Jonathan Sprangler; Rory Schermerhorn

(57) ABSTRACT

An implant installation device is provided for delivering an implant to a target implantation site including a handle with a first and second arms extending distally therefrom. A translation member extends through the handle such that a distal portion lies between the first arm and second arm while a proximal portion extends beyond the proximal end of the handle. An inserter is coupled at the distal end of the translation member and also lies between the first arm and second arm. With an implant positioned proximate the distal end of the inserter, the distal ends of the arms may be inserted between the pair of vertebrae. The translation member may be operated to drive the inserter distally, which in turn pushes the implant toward the implantation site.

14 Claims, 9 Drawing Sheets

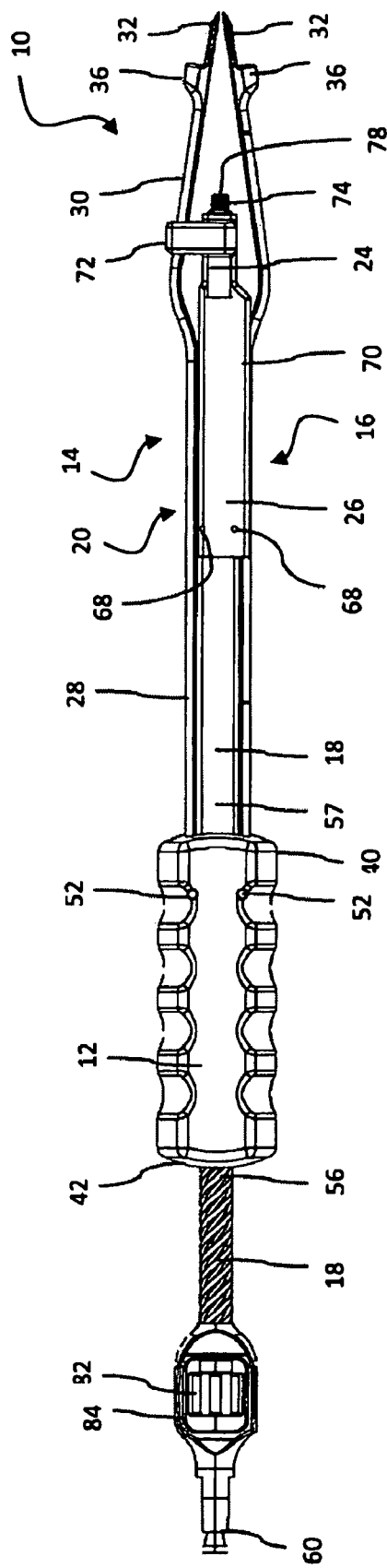
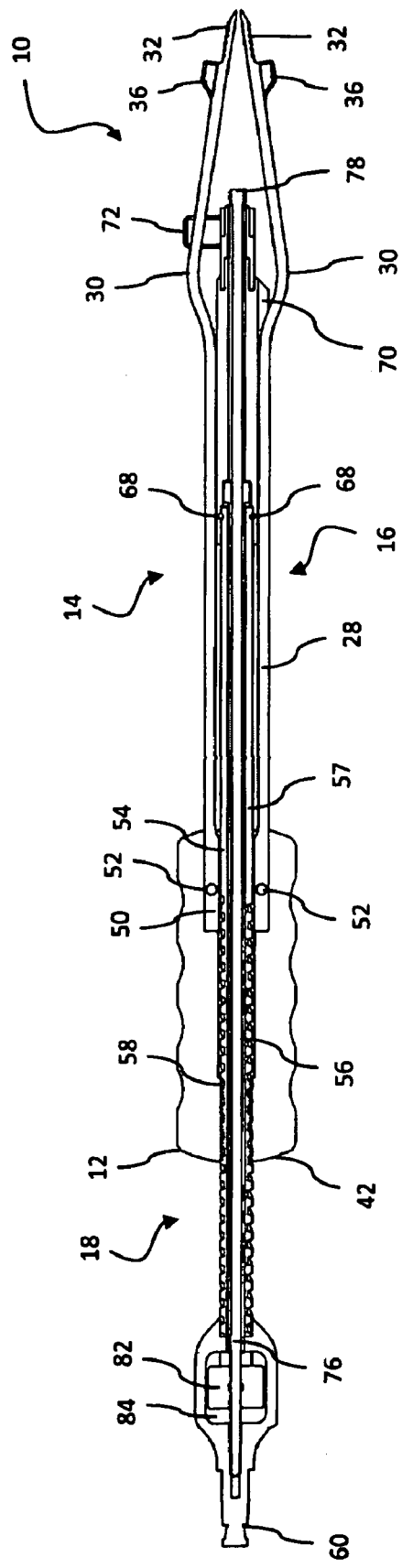
FIG. 2
FIG. 3

SPINAL IMPLANT INSTALLATION DEVICE

CROSS REFERENCES TO RELATED APPLICATIONS

The present application is a nonprovisional patent application claiming benefit under 35 U.S.C. §119(e) from commonly owned and U.S. Provisional Application Ser. No. 61/028,886, entitled "Spinal Distraction and Implantation Assembly and Related Methods," filed on Feb. 15, 2008, and commonly owned and U.S. Provisional Application Ser. No. 61/105,384, entitled "Spinal Distraction and Implantation Assembly & Related Methods," filed on Oct. 14, 2008, the entire contents of which are each hereby expressly incorporated by reference into this disclosure as if set forth fully herein.

BACKGROUND OF THE INVENTION

I. Field of the Invention

The present invention relates generally to delivering and implanting spinal implants during surgery.

II. Discussion of the Prior Art

The spine is formed by a column of vertebra that extends between the cranium and pelvis and includes three major regions known as the cervical, thoracic and lumbar regions. There are 7 cervical vertebrae, 12 thoracic vertebrae, and 5 lumbar vertebrae. These vertebrae are separated from one another by intervertebral discs that act as shock absorbers and allow the vertebrae to move relative to each other. A series of approximately 9 fused vertebrae extend from the lumbar region and make up the sacral and coccygeal regions of the vertebral column.

The main functions of the spine are to provide skeletal support and protect the spinal cord. If the normal physiology of the spine is disrupted due to trauma, degeneration, or other ailments, the delicate nervous tissue proximate the spine may be affected and the patient may experience symptoms ranging from discomfort to paralysis. In such instances surgical correction is often performed to relieve, or at least reduce, the patient's symptoms. Often times the surgical correction involves positioning an implant into the intervertebral space. This generally provides support and restores a more natural height to the disc space. The implants may be designed to provide a scaffold for bone ingrowth between the vertebra (i.e. fusion implant) or the implants may be designed to replace the function of the intervertebral disc (i.e. partial or total disc replacement).

SUMMARY OF THE INVENTION

The present disclosure is directed at an implant installation device for delivering an implant to a target site between a pair of vertebrae. The installation device includes a handle with a first arm and a second arm fixed to the handle and extending distally therefrom. A translation member is coupled to the handle and extends through the handle such that a distal portion lies between the first arm and second arm while a proximal portion extends beyond the proximal end of the handle. An inserter is coupled at the distal end of the translation member and also lies between the first arm and second arm. With an implant positioned proximate the distal end of the inserter, the distal ends of the arms may be inserted between the pair of vertebrae. The translation member may be operated to drive the inserter distally, which in turn pushes the implant forward (toward the disc space) between the arms until the implant enters the intervertebral disc space.

The first and second arms may form a parallel region proximate the handle, in which the first arm and second arm are generally parallel to one another, and a non-parallel region proximate the distal end, in which the arms converge towards each other. The distal ends of arms form distraction tangs. Because the distraction tangs converge at the distal end they may be easily advanced between the vertebrae without requiring prior distraction of the disc space. As the implant is advanced forward through the non-parallel region, the height of the implant will force the arms to flex apart such that the distraction tangs (positioned between the vertebrae) will impart a separation force to the vertebrae and distract the disc space just enough to allow entry of the implant. Each distraction tang may be provided with surface features along the outer surface to enhance engagement with the vertebral endplates and prevent slippage or unwanted movement when the distraction tangs are positioned in the disc space. By way of example only, the surface features may include grooves, ridges, and/or teeth situated on at least a portion of the outer surface. Separating the distraction tangs from the rest of the arms is an abutment protruding vertically away from the respective arm. The abutment acts as a stopper, limiting the depth to which the distraction tangs may be inserted into the intervertebral space. This prevents the distraction tangs from inadvertently being advanced beyond the opposing limits of the disc space, as well as to control the final positioning of the implant. A notch in the center of each abutment provides a sightline to the vertebral bodies when the distraction tangs are inserted into the intervertebral space up to the abutment.

The handle includes a distal end, a proximal end, and a central bore extending the length of the handle. The central bore includes first engagement region for coupling with the translation member and a second engagement region for coupling to the first and second arms. First and second arms may be connected to each other at a distal arm body which is dimensioned to be snugly received within the second engagement region of the handle. Pins positioned in complementary pin holes formed through the handle and distal arm body fix the arms to the handle. The distal arm body includes a bore in communication with the central bore of the handle at one end, and opening into a space between the first arm and second arm at the other end. The bore is dimensioned to pass the translation member there through such that the translation member may extend from beyond the distal end of the handle through the bores and into the space between the first arm and second arm.

At least a portion of the translation member may include an exterior thread. A complementary interior thread is situated in the first engagement region of the handle in order to movably couple the translation member to the handle. The interior thread and exterior thread engage such that rotation of the translation member causes the translation member to move forward (distally) or backward (proximally) depending on the direction of rotation. In one embodiment, the exterior thread stops proximally to the distal portion forming a non-threaded region. The non-threaded region may be provided of a length configured to stop backward movement of the inserter in a position where the implant, when attached, is located adjacent to the parallel region, at the proximal end of the non-parallel region. By starting the implant at this relatively forward position, the distance the implant must travel is minimal, reducing the time and effort required position the implant. A universal connector, such as, for example, a Hudson connector, may be provided at the proximal end of the translation member to allow the attachment of accessories used to aid in imparting rotation to the translation member (e.g. T-handles, gearshift handles, etc. . . . , not shown).

The inserter, including a forward body and a trailing body, is situated in the space between the first arm and the second arm. At the proximal end of the trailing body, the inserter is rotationally coupled to the translation member. That is, the translation member is longitudinally fixed to the trailing body such that forward or backward movement of the translation member will cause the inserter to move in the same direction while permitting the translation member to rotate freely relative to the inserter. To accomplish this, by way of example only, the trailing body may include a bore opening at the proximal end of the trailing body and dimensioned to receive a distal portion of the translation member. The distal portion of the translation member may include a radial groove situated therein. Pins (not shown) positioned through pin holes engage the radial groove, denying longitudinal movement between the inserter and translation member while allowing for free rotation there between.

The trailing body of the inserter is dimensioned to slidably engage the inner surface of the first arm and second arm along the parallel region, having a height approximating the distance between the inner surfaces of the first arm and second arm in the parallel region. At least one pair of guide rails extend vertically from the trailing body capturing the sides of arm there between. The guide rails stabilize an arm, providing a counter-torque when the translation member is rotated to advance the inserter and ensuring that the inserter tracks forward smoothly and in-line with the arms. The length of the trailing body and the guide rails that extend along the arm is such that at least of portion of the parallel-region is still situated between the guide rails when the translation member is advanced to the most distal position.

The forward body of the inserter includes a pair of guide posts that extend vertically on either side of the arm, capturing the sides of arm there between. The guide posts stabilize the arm, providing a counter-torque when the translation member is rotated and again ensuring that the inserter tracks forward smoothly and in-line with the arms. The guide posts are generally taller than the guide rails because the guide posts engage the arm in the non-parallel region that is subject to greater height variation as the implant is advanced towards the disc space. Additionally, the guide posts are adapted to engage a face of one of the vertebra when the inserter is fully advanced to deposit implant in the disc space. By engaging the vertebra, the guide posts help facilitate the ejection of the distraction tangs from the disc space without bothering the position of the implant. As the implant enters the disc space and approaches the final desired position, the guide posts engage the vertebra preventing any further advancement of the inserter. Further rotation of the translation member thus causes the handle to move proximally, pulling the distraction tangs out of the disc space. In alternate embodiments, the guide posts may be situated in various other arrangements. By way of example, an additional pair of guide posts may extend vertically in the opposite direction from the first guide posts such that guides posts capture both arms there between. Alternatively, or in addition thereto, the guide posts may be connected by a cross bar situated above and/or below one or both of arms. The cross bar may further include a forward facing protrusion configured to engage the vertebral body instead of the guide post to effect removal of the distraction tangs.

Preferably, the implant is temporarily attached in position in front of the inserter. An implant holder may be included to hold the implant in place during insertion. As shown, by way of example, the implant holder comprises a rod extending though a bore in the translation member. The rod is freely rotatable through the bore and includes a threaded end extending beyond the distal end of the forward body and configured to engage a complementary threaded receiving aperture on the implant. To temporarily fix the implant to the device the implant is held in front of the threaded end and the rod is rotated until the threads of threaded end mate with the threaded receiving aperture. To assist in rotating the rod, a thumbwheel may be attached to a proximal portion of the rod. As shown, a thumbwheel housing may be formed in the end of the translating member to house the thumbwheel. While the implant holder has been described as utilizing a threaded connection to the implant, it will be appreciated that other attachment arrangements, such as for example, clamping or fork type arrangements may be used without departing from the scope of the present invention.

The implant insertion device is used in a surgical procedure to position an implant between a pair of vertebral bodies. An access corridor is first created providing an avenue for delivering the insertion device and the implant attached thereto, to the intervertebral target site. Once the access corridor is formed, the disc space may be prepared using conventional disc space preparation techniques and instruments, such as, for example, rasps, ronguers, curettes, etc. . . . . . The appropriate sized implant may then be attached to the inserter using the implant holder and the installation device may be passed through the operative corridor to the target spinal level. The distraction tangs may then be inserted into the disc space between the vertebrae until the abutments rest against the faces of the vertebral bodies. The surface features on the distraction tangs will engage the vertebral end plates and help keep the distraction tangs in the desired position. With the distraction tangs positioned in the disc space and the abutments resting on the vertebral bodies, the translation member may by operated to advance the inserter forward toward the disc space. When the translating member is rotated, the exterior threads advance along the interior threads inside the handle and thus moving the translating member relative to the handle. As the translating member moves forward toward the disc space the inserter also moves forward driving the implant though the non-parallel region of the arms. As the implant moves forward the height of the implant exerts a force on the arms causing them to flex away from each other. The distraction force is delivered to the vertebral bodies via the distraction tangs and the disc space is distracted to a height determined by the height of the implant. The distraction tangs also act as a guard to the vertebral endplates, preventing gouging or other damage that could occur if the implant was forced into the disc space in direct contact with endplates.

As the implant is fully received within the disc space, the guide posts come into contact with the upper vertebral body. With the guide posts in contact with the vertebral body, additional advancement of the translating member causes the handle and arms to move backward relative to the inserter withdrawing the distraction tangs from the disc space. Once the distraction tangs are free from the disc space, the implant holder may be released from the implant and the implant installation device may be removed from the operative corridor, which may be subsequently closed.

Although the implant installation device is described herein in use through an anterior approach, it will be appreciated that the device may be utilized to access the spine using other approaches (e.g. anterolateral, lateral, posterolateral, and posterior approaches). Also the implant may utilized to access the spine in any of the different spinal regions. To accommodate the different anatomies (e.g. size, etc. . . . ) found in the different spinal regions, the dimensions of the device may be adjusted accordingly, for the device as a whole or for any individual or combination of individual components and/or features. Similarly, the dimensions of the device may adjusted for the device as a whole or for any individual or combination of individual components and/or features, as appropriate for the desired approach. It will also be appreciated that the implant to be delivered, including the size and footprint may vary according to the spinal region and desired approach.

According to an alternative embodiment of the present invention, the implant installation device may be configured for use through a surgical corridor formed via a lateral approach to the spine. According to this embodiment, distraction tangs may be detachably coupled to the first and second arms. By detachably coupling the distraction tangs to the first and second arms, distraction tangs of various sizes may be utilized based on the particular anatomy of the patient. This may be particularly advantageous, for example, when the installation device is utilized to deliver an implant configured for lateral insertion due to a relatively large range of length dimensions associated with lateral implants. As previously mentioned, the distraction tangs act as a guard when they are situated between the implant and the vertebral endplate. Closely matching the length of the distraction tangs to the length of the selected implant may reduce the risk of endplate damage during implant delivery, while also ensuring that the distraction tangs are not long enough to extend completely through the intervertebral disc space.

Any of a number of configurations may be utilized to detachably couple the distraction tangs to the first and second arms. By way of example only, abutments may include a grooves extending laterally across the face of the abutments. As shown, the grooves are a dovetail grooves. A complementary notch or ridge situated on the proximal end of each distraction tang may be slidably received within the grooves. Stop(s) may be provided on any of or any combination of the distraction tang and the notch to prevent the distraction tangs from sliding all the way through grooves. According to one example, to temporarily fix the distraction tangs to the arms, the abutments may be further provided with apertures in open communication with the grooves. Setscrews may be advanced through the apertures such that they may engage the notches, locking the distraction tangs in position.

The non-parallel region of the arms may be longer than that of the device to better accommodate the lateral approach. Rather than extending outward first and then converging together sharply to create space for the implant in the relatively short non-parallel region of the installation device, the non-parallel region of installation device is extended and the arms converge towards each other directly. This creates a sleeker profile and allows the installation device to be advanced through smaller corridors (such as for example, retraction and/or distraction assemblies used to access the lateral aspect of the spine).

BRIEF DESCRIPTION OF THE DRAWINGS

The invention will be more fully understood from the following detailed descriptions taken in conjunction with the accompanying drawings, in which:

FIG. 2 is a side view of the implant installation device of FIG. 1, according to one example embodiment;

FIG. 3 is a cross-section of the side view of implant installation device as shown in FIG. 2, according to one example embodiment;

DESCRIPTION OF THE PREFERRED EMBODIMENT

Figure 1:
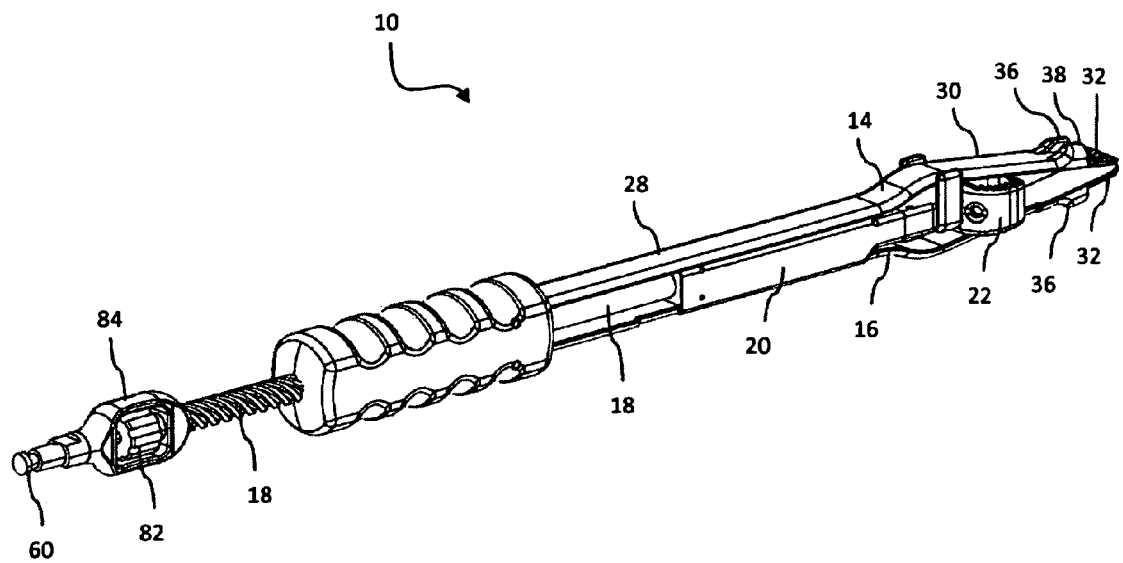
FIG. 1 is a perspective view of an implant installation device with an implant coupled thereto, according to one example embodiment.
Figure 4:
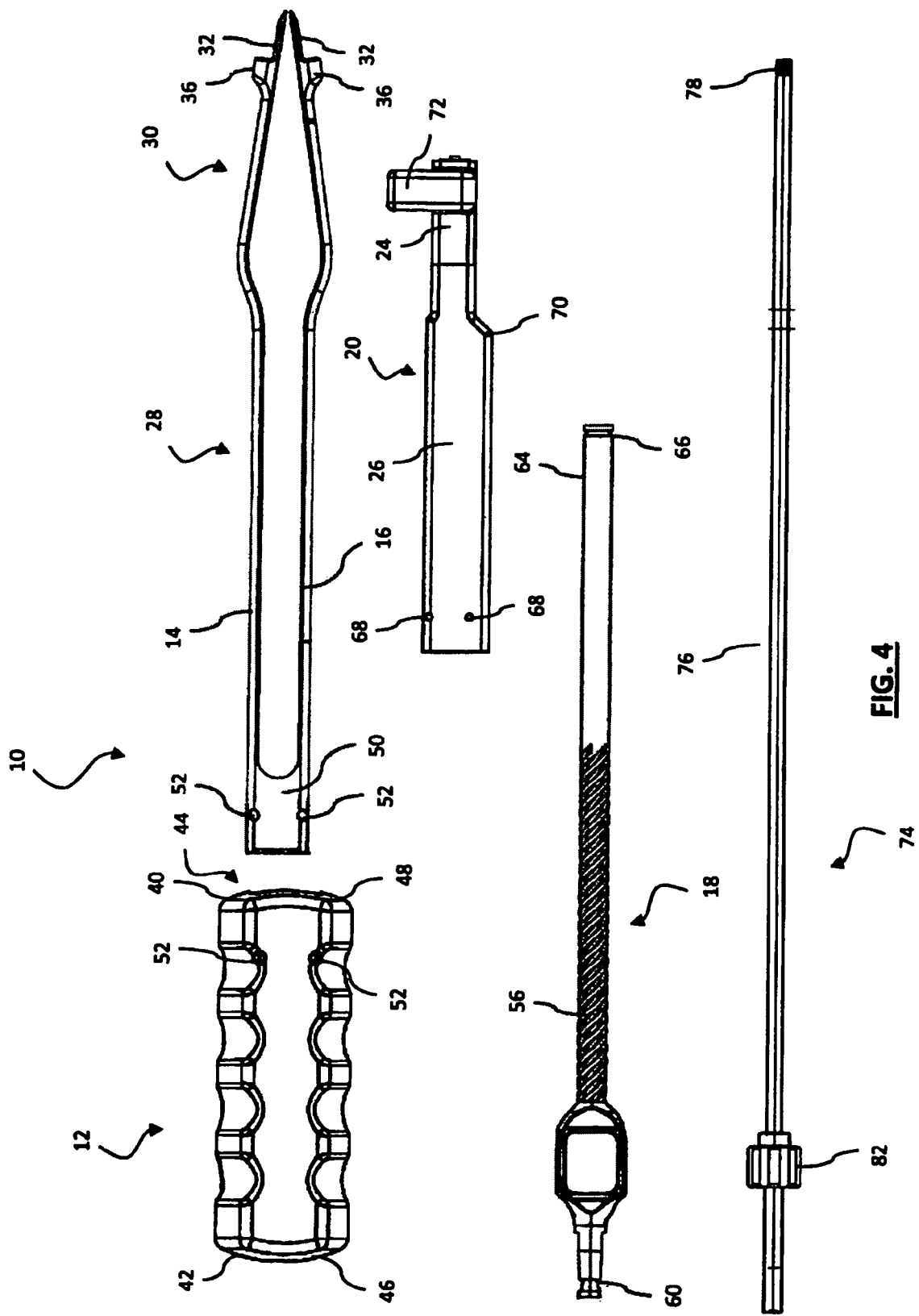
FIG. 4 is an exploded side view of the implant installation device of FIG. 1, according to one example embodiment.
Figure 5:
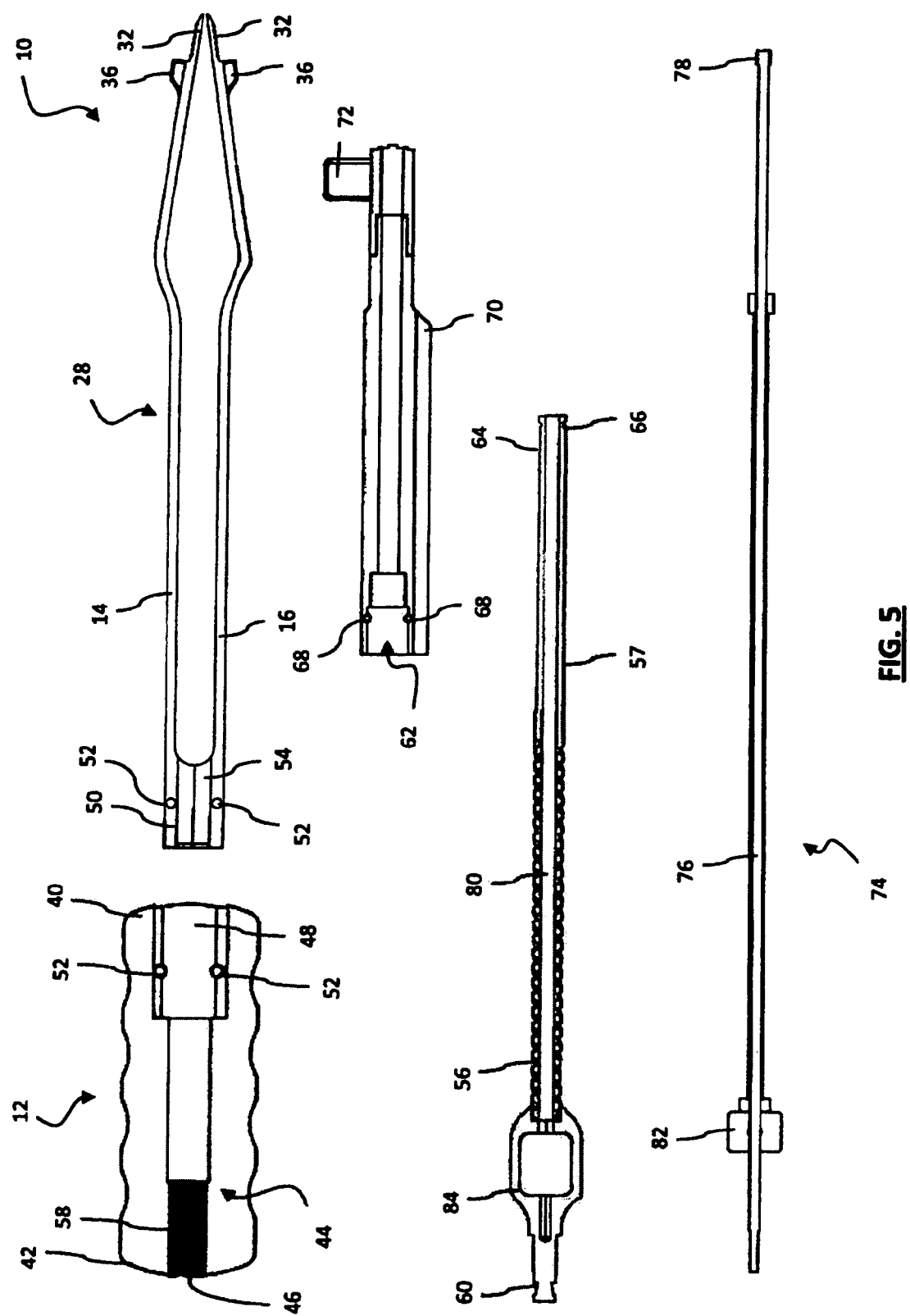
FIG. 5 is a cross-section of the exploded side view of implant installation device as shown in FIG. 4, according to one example embodiment.
Figure 6:
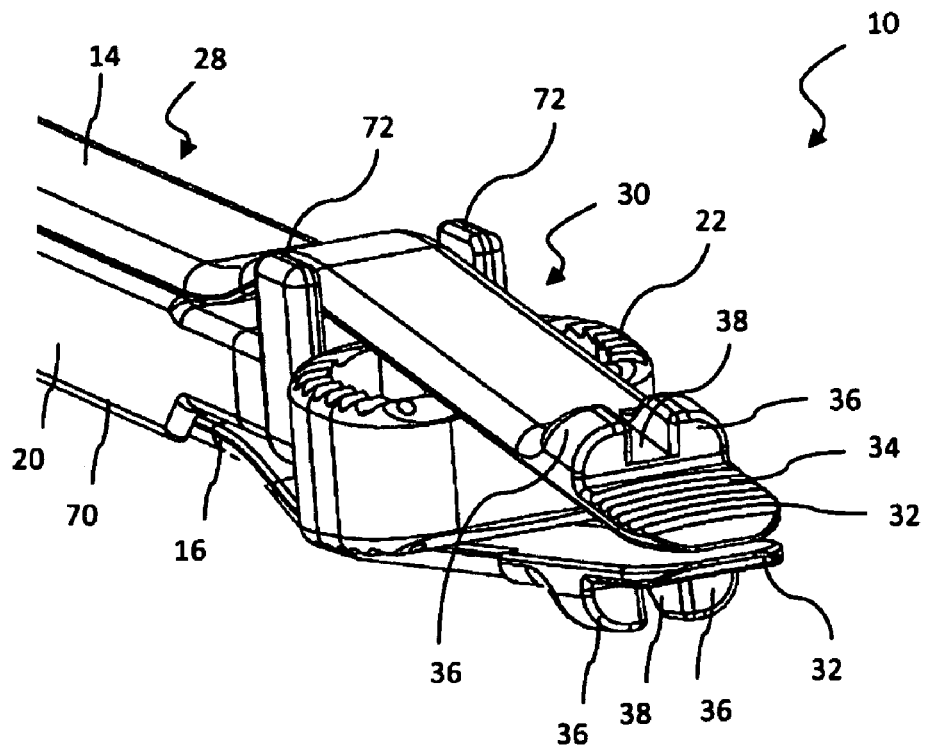
FIG. 6 is a perspective view of a distal end of the implant installation device of FIG. 1 with an implant coupled thereto, according to one example embodiment.
Figure 7:
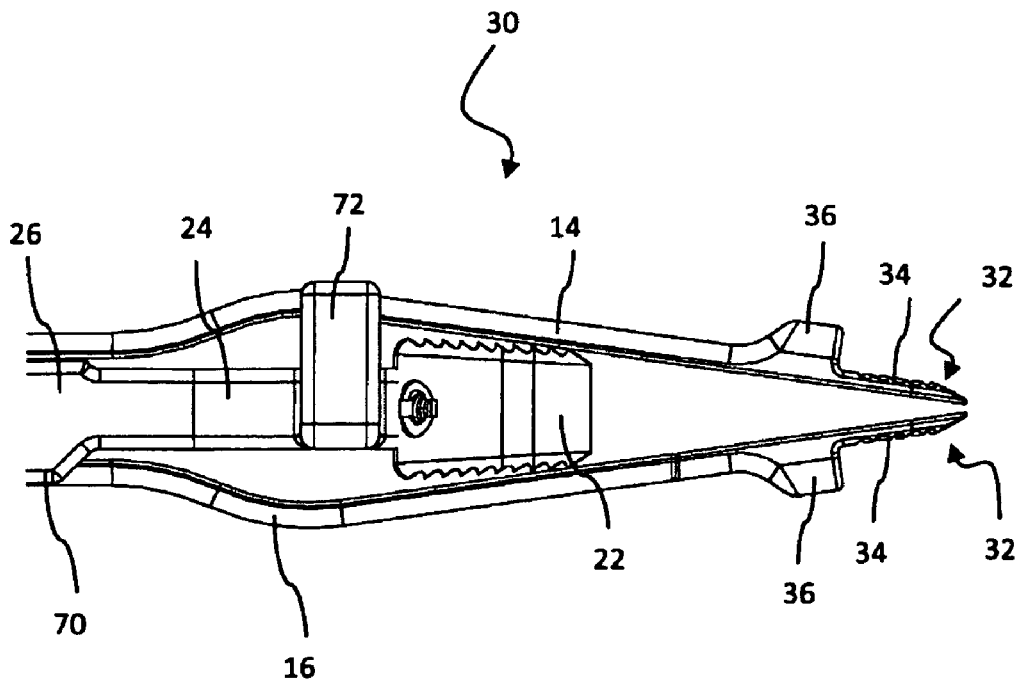
FIG. 7 is a side view of the distal end of the implant installation device as shown in FIG. 7, according to one example embodiment.

Illustrative embodiments of the invention are described below for the purposes of understanding the principles of the invention. No limitation of the scope of the invention is therefore intended. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The device disclosed herein boasts a variety of inventive features and components that warrant patent protection, both individually and in combination.

FIGS. 1-7 illustrate, according to one example embodiment, an implant installation device 10 for delivering an implant to a target site between a pair of vertebrae. The installation device 10 includes a handle 12 with a first arm 14 and a second arm 16 fixed to the handle 18 and extending distally therefrom. A translation member 18 is coupled to the handle 18 and extends through the handle such that a distal portion lies between the first arm 14 and second arm 16 while a proximal portion extends beyond the proximal end of the handle. An inserter 20 is coupled at the distal end of the translation member 18 and also lies between the first arm 14 and second arm 16. With an implant 22 positioned proximate the distal end of the inserter 20 the distal ends of the arms 14, 16 may be inserted between the pair of vertebrae. The translation member 18 may be operated to drive the inserter 20 distally, which in turn pushes the implant 22 forward (toward the disc space) between the arms 14, 16 until the implant enters the intervertebral disc space. By way of example only, the implant 22 may comprise one of the implants shown and described in the commonly owned and co-pending U.S. patent application Ser. No. 11/526,421, entitled, "Spinal Fusion Implant and Related Methods," filed on Sep. 25, 2006, the entire contents of which is expressly incorporated by reference as if set forth fully herein.

The interaction between the various components of the installation device may be best appreciated with reference to FIGS. 2-5. The first and second arms 16 may form a parallel region 28 proximate the handle 18, in which the first arm 14 and second arm 16 are generally parallel to one another, and a non-parallel region 30 proximate the distal end, in which the arms 14, 16 converge towards each other. The distal ends of arms 14, 16 form distraction tangs 32. Because the distraction tangs 32 converge at the distal end they may be easily advanced between the vertebrae without requiring prior distraction of the disc space. As the implant is advanced forward through the non-parallel region 30, the height of the implant will force the arms 14, 16 to flex apart such that the distraction tangs 32 (positioned between the vertebrae) will impart a separation force to the vertebrae and distract the disc space just enough to allow entry of the implant. As best viewed in FIG. 6, each distraction tang 32 may be provided with surface features 34 along the outer surface to enhance engagement with the vertebral endplates and prevent slippage or unwanted movement when the distraction tangs 32 are positioned in the disc space. By way of example only, the surface features 34 may include grooves, ridges, and/or teeth situated on at least a portion of the outer surface. Separating the distraction tangs 32 from the rest of the arms 14, 16 is an abutment 36 protruding vertically away from the respective arm 14 or 16. The abutment 36 acts as a stopper, limiting the depth to which the distraction tangs 32 may be inserted into the intervertebral space. This prevents the distraction tangs 32 from inadvertently being advanced beyond the opposing limits of the disc space, as well as to control the final positioning of the implant. A notch 38 in the center of each abutment 36 provides a sightline to the vertebral bodies when the distraction tangs 32 are inserted into the intervertebral space up to the abutment 36.

The handle 12 includes a distal end 40, a proximal end 42, and a central bore 44 extending the length of the handle 12. The central bore 44 includes first engagement region 46 for coupling with the translation member 18 and a second engagement region 48 for coupling to the first and second arms 14, 16. First and second arms 14, 16 may be connected to each other at a distal arm body 50 which is dimensioned to be snugly received within the second engagement region 48 of the handle 12. Pins (not shown) positioned in complementary pin holes 52 formed through the handle 12 and distal arm body 50 fix the arms to the handle. Distal arm body 50 includes a bore 54 in communication with the central bore 44 of the handle 12 at one end, and opening into a space between the first arm 14 and second arm 16 at the other end. The bore 54 is dimensioned to pass the translation member 18 there through such that the translation member 18 may extend from beyond the distal end 42 of the handle 12 through the bores 44 and 54 and into the space between the first arm 14 and second arm 16.

According to this example embodiment, at least a portion of the translation member 18 includes an exterior thread 56. A complementary interior thread 58 is situated in the first engagement region 46 of the handle 12 in order to movably couple the translation member 18 to the handle. Interior thread 58 and exterior thread 56 engage such that rotation of the translation member 18 causes the translation member 18 to move forward (distally) or backward (proximally) depending on the direction of rotation. In one embodiment, the exterior thread 56 stops proximally to distal portion 64 forming a non-threaded region 57. The non-threaded region may be provided of a length configured to stop backward movement of the inserter in a position where the implant 22, when attached, is located adjacent to the parallel region 28, at the proximal end of the non-parallel region 30. By starting the implant at this relatively forward position, the distance the implant must travel is minimal, reducing the time and effort required position the implant. A universal connector 60, such as, for example, a Hudson connector, may be provided at the proximal end of the translation member 18 to allow the attachment of accessories used to aid in imparting rotation to the translation member 18 (e.g. T-handles, gearshift handles, etc. . . . , not shown).

The inserter 20, including a forward body 24 and a trailing body 26, is situated in the space between the first arm 14 and the second arm 16. At the proximal end of the trailing body 26, the inserter 20 is rotationally coupled to the translation member 18. That is, the translation member 18 is longitudinally fixed to the trailing body 26 such that forward or backward movement of the translation member 18 will cause the inserter 20 to move in the same direction while permitting the translation member 18 to rotate freely relative to the inserter 20. To accomplish this, by way of example only, the trailing body 26 may include a bore 62 opening at the proximal end of the trailing body and dimensioned to receive a distal portion 64 of the translation member 18. The distal portion 64 of the translation member 18 may include a radial groove 66 situated therein. Pins (not shown) positioned through pin holes 68 engage the radial groove 66, denying longitudinal movement between the inserter 20 and translation member 18 while allowing for free rotation there between.

The trailing body 26 of the inserter 20 is dimensioned to slidably engage the inner surface of the first arm 14 and second arm 16 along the parallel region 28, having a height approximating the distance between the inner surfaces of the first arm 14 and second arm 16 in the parallel region 28. At least one pair of guide rails 70 extend vertically from the trailing body 26 capturing the sides of arm 16 there between. The guide rails 70 stabilize arm 16, providing a counter-torque when the translation member 18 is rotated to advance the inserter 20 and ensuring that the inserter 20 tracks forward smoothly and in-line with the arms 14, 16. The length of the trailing body 26 and the guide rails 70 that extend along the arm 16 is such that at least of portion of the parallel-region 28 is still situated between the guide rails 70 when the translation member 80 is advanced to the most distal position. If a single pair of guide rails 70 is utilized, as pictured in the embodiment of FIG. 1, the guide rails 70 should extend in a direction opposite the guide posts 72, described below, such that both arms 14 and 16 are captured by guide elements of the inserter 20.

The forward body 24 of the inserter 20 includes a pair of guide posts 72 that extend vertically on either side of the arm 14, capturing the sides of arm 14 there between. The guide posts 72 stabilize the arm 14, providing a counter-torque when the translation member 18 is rotated and again ensuring that the inserter 20 tracks forward smoothly and in-line with the arms 14, 16. The guide posts 72 are generally taller than the guide rails 70 because the guide posts engage the arm 14 in the non-parallel region 30 that is subject to greater height variation as the implant 22 is advanced towards the disc space. Additionally, the guide posts 72 are adapted to engage a face of one of the vertebra when the inserter 20 is fully advanced to deposit implant in the disc space. By engaging the vertebra, the guide posts 72 help facilitate the ejection of the distraction tangs 32 from the disc space without bothering the position of the implant. As the implant 22 enters the disc space and approaches the final desired position, the guide posts 72 engage the vertebra preventing any further advancement of the inserter 20. Further rotation of the translation member 18 thus causes the handle 12 to move proximally, pulling the distraction tangs 32 out of the disc space. In alternate embodiments, the guide posts 72 may be situated in various other arrangements. By way of example, an additional pair of guide posts may extend vertically in the opposite direction from the first guide posts such that guides posts capture both arms 14 and 16 there between. Alternatively, or in addition thereto, the guide posts 72 may be connected by a cross bar situated above and/or below one or both of arms 14, 16. The cross bar may further include a forward facing protrusion configured to engage the vertebral body instead of the guide post to effect removal of the distraction tangs 32.

Preferably, the implant 22 is temporarily attached in position in front of the inserter 20. An implant holder 74 may be included to hold the implant in place during insertion. As shown, by way of example, the implant holder comprises a rod 76 extending though a bore 80 in the translation member 18. The rod 76 is freely rotatable through the bore 80 and includes a threaded end 78 extending beyond the distal end of the forward body 24 and configured to engage a complementary threaded receiving aperture (not shown) on the implant 22. To temporarily fix the implant to the device 10 the implant is held in front of the threaded end 78 and the rod 76 is rotated until the threads of threaded end 78 mate with the threaded receiving aperture. To assist in rotating the rod 76, a thumbwheel 82 may be attached to a proximal portion of the rod 76. As shown, a thumbwheel housing 84 may be formed in the end of the translating member 18 to house the thumbwheel 82. While the implant holder has been described as utilizing a threaded connection to the implant 22, it will be appreciated that other attachment arrangements, such as for example, clamping or fork type arrangements may be used without departing from the scope of the present invention.

Figure 8:
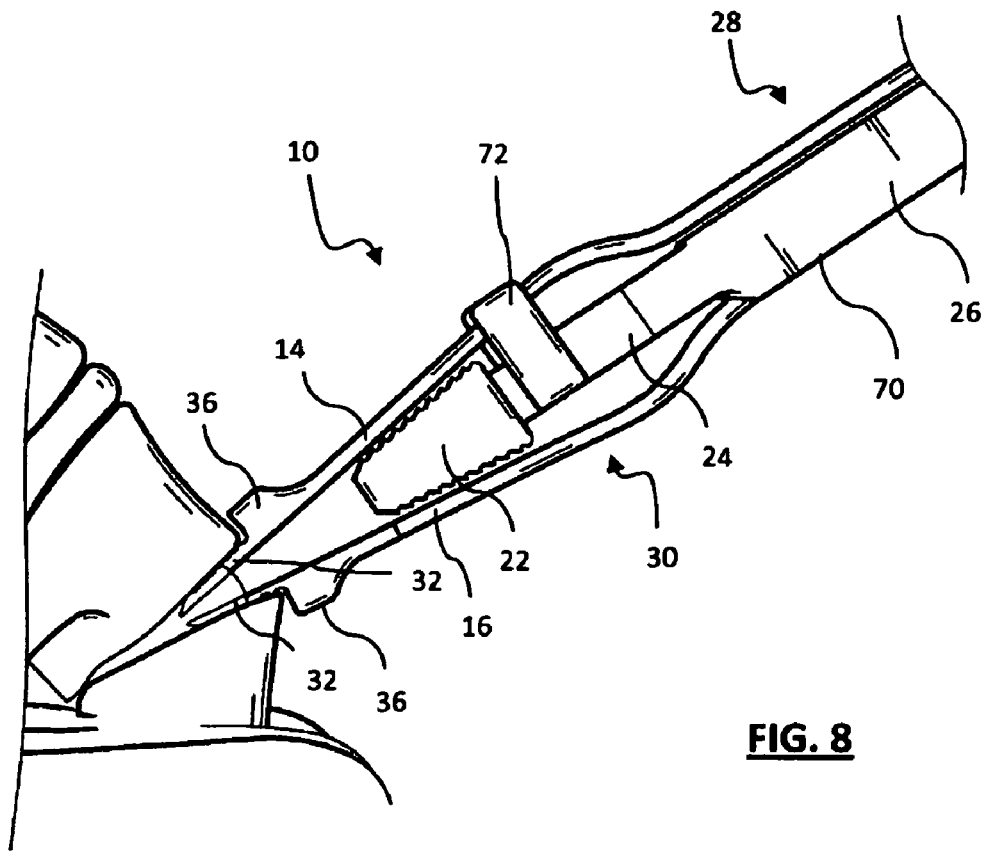
FIGS. 8-11 are side views illustrating steps performed during use of the implant installation device of FIG. 1, according to one example embodiment.
Figure 9:
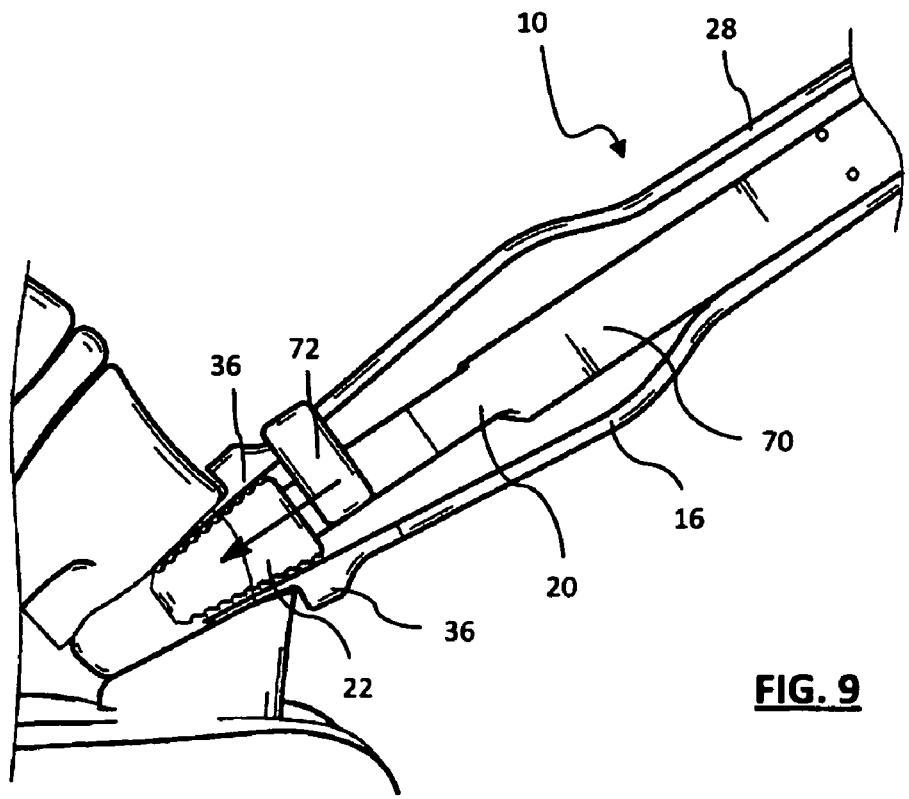
Figure 10:
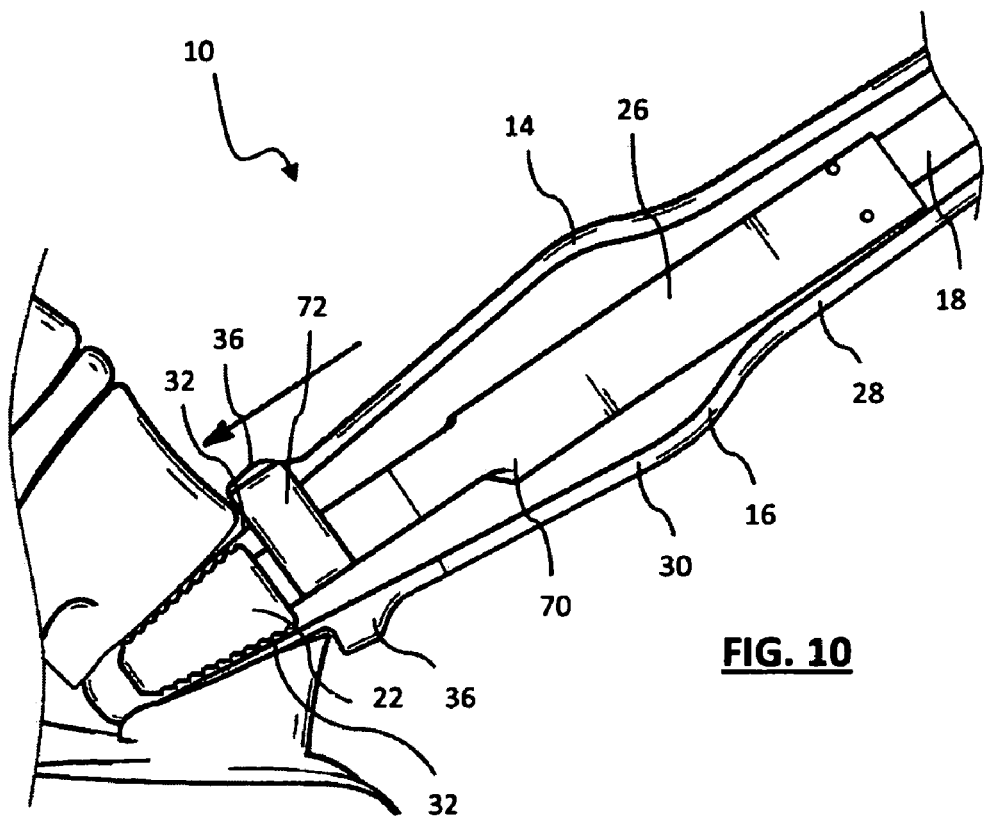

With reference to FIGS. 8-11, one surgical procedure utilizing the implant insertion device 10 to position an implant 22 between a pair of vertebrae will now be described. An access corridor is first created providing an avenue for delivering the insertion device 10 and the implant 22 attached thereto, to the intervertebral target site. By way of example only, FIGS. 8-10 illustrate the insertion device being used to deliver an implant through an anterior approach to the spine and the implant 22 is configured for such an approach. Once the access corridor is formed, the disc space may be prepared using conventional disc space preparation techniques and instruments, such as, for example, rasps, ronguers, curettes, etc. . . . . The appropriate sized implant 22 may then be attached to the inserter 20 using the implant holder 74 and the installation device 10 may be passed through the operative corridor to the target spinal level. The distraction tangs 32 may then be inserted into the disc space between the vertebrae until the abutments 36 rest against the faces of the vertebral bodies, as depicted in FIG. 8. The surface features 34 on the distraction tangs will engage the vertebral end plates and help keep the distraction tangs 32 in the desired position. With the distraction tangs 32 positioned in the disc space and the abutments 36 resting on the vertebral bodies, the translation member 18 may by operated to advance the inserter 20 forward toward the disc space. When the translating member 18 is rotated, the exterior threads 56 advance along the interior threads 58 inside the handle 12 and thus moving the translating member 18 relative to the handle 12. As the translating member 18 moves forward toward the disc space the inserter 20 also moves forward driving the implant 22 though the non-parallel region 30 of the arms 14, 16, As, the implant 22 moves forward (FIG. 9) the height of the implant exerts a force on the arms 14, 16 causing them to flex away from each other. The distraction force is delivered to the vertebral bodies via the distraction tangs 32 and the disc space is distracted to a height determined by the height of the implant 22. The distraction tangs 32 also act as a guard to the vertebral endplates, preventing gouging or other damage that could occur if the implant 22 was forced into the disc space in direct contact with endplates.

Figure 11:
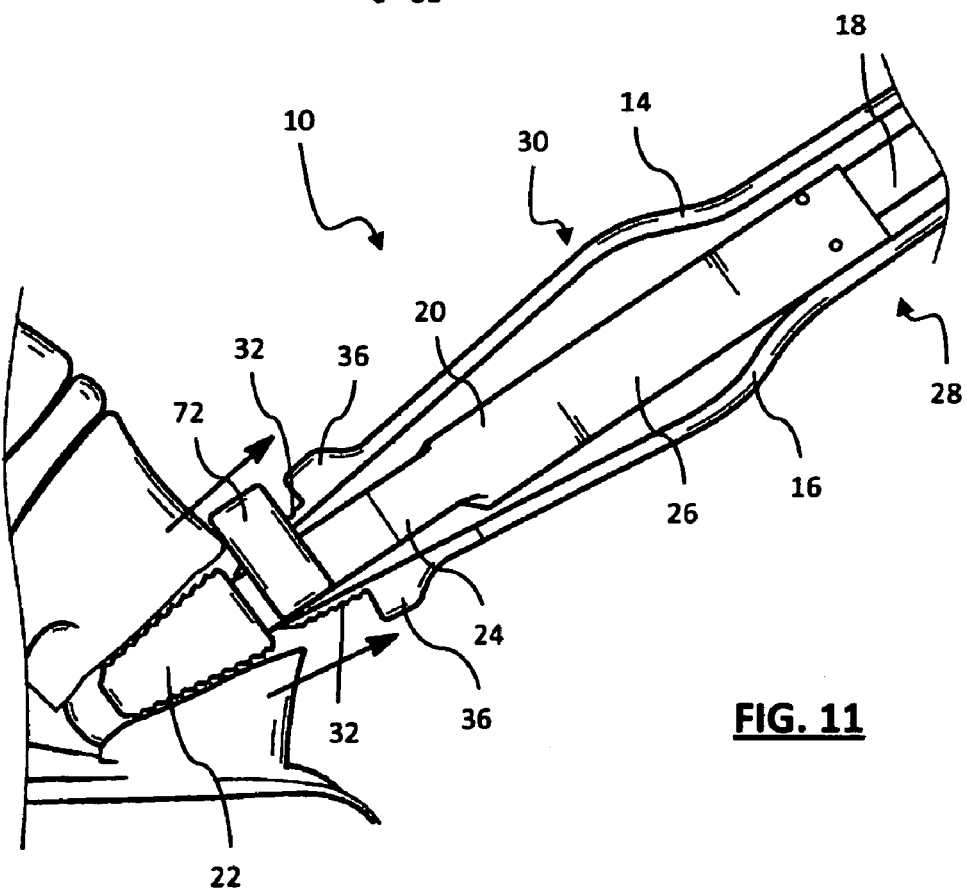

As the implant 22 is fully received within the disc space, the guide posts 72 come into contact with the upper vertebral body, as shown in FIG. 10. With the guide posts 72 in contact with the vertebral body, additional advancement of the translating member 18 causes the handle 12 and arms 14, 16 to move backward relative to the inserter 20 withdrawing the distraction tangs 32 from the disc space, as illustrated in FIG. 11. Once the distraction tangs 32 are free from the disc space, the implant holder 74 may be released from the implant 22 and the implant installation device may be removed from the operative corridor, which may be subsequently closed.

While the example embodiment of the implant installation device 10 was shown above in use through an anterior approach, it will be appreciated that the device may be utilized to access the spine using other approaches (e.g. anterolateral, lateral, posterolateral, and posterior approaches). Also the implant may utilized to access the spine in any of the different spinal regions. To accommodate the different anatomies (e.g. size, etc. . . . ) found in the different spinal regions, the dimensions of the device may be adjusted accordingly, for the device as a whole or for any individual or combination of individual components and/or features. Similarly, the dimensions of the device may adjusted for the device as a whole or for any individual or combination of individual components and/or features, as appropriate for the desired approach. It will also be appreciated that the implant to be delivered, including the size and footprint may vary according to the spinal region and desired approach.

Figure 12:
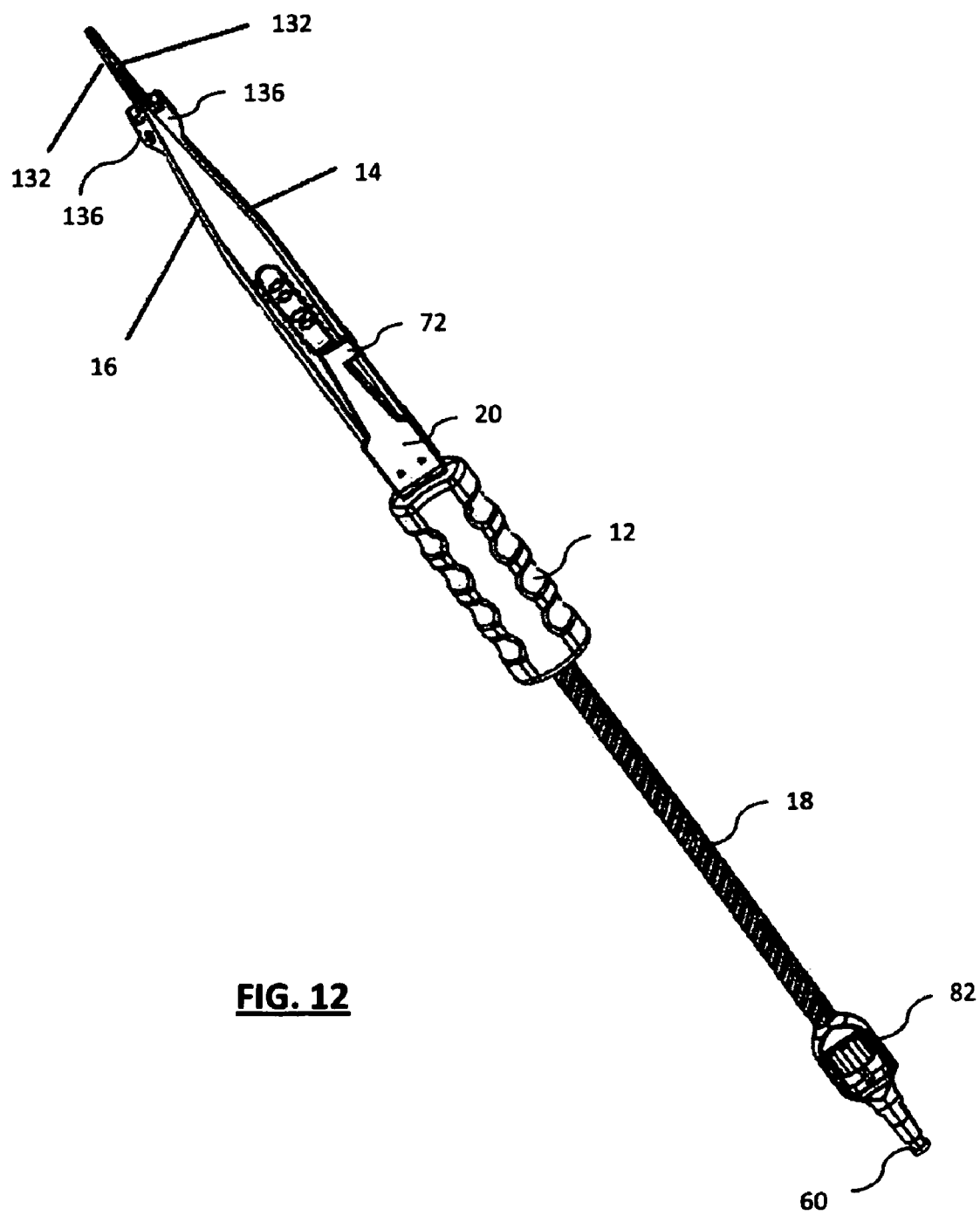
FIG. 12 is a is a perspective view of an implant installation device with an implant coupled thereto, according to another example embodiment.
Figure 13:
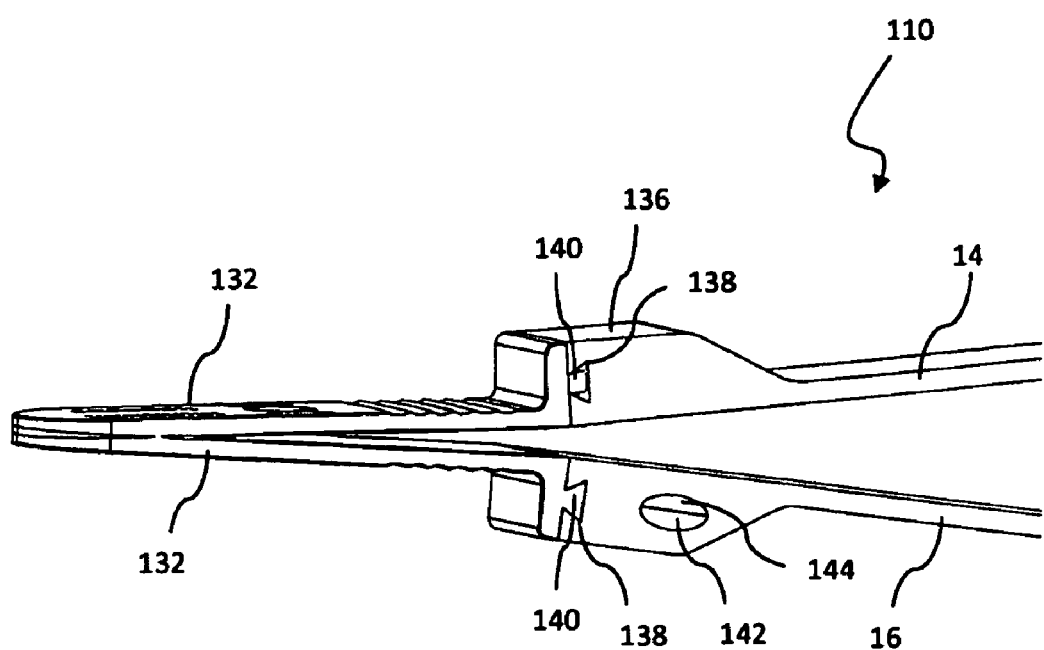
FIG. 13 is a side view of the distal end of the implant installation device of FIG. 12, according to one example embodiment.

By way of example, another example embodiment is shown in FIGS. 12 and 13. The implant installation device 110, shown in FIGS. 12 and 13 shares many common elements with the installation device 10 such that repeat discussion of the common elements is unnecessary. For simplicity, identical callouts have been used to common elements. The dimensions of installation device 110 have been slightly modified as compared to the installation device 10 to better configure the implant installation device 110 for use through a surgical corridor formed via a lateral approach to the spine. According to this embodiment, distraction tangs 132 may be detachably coupled to the first and second arms 14, 16. By detachably coupling the distraction tangs 132 to the first and second arms 14, 16, distraction tangs 132 of various sizes may be utilized based on the particular anatomy of the patient. This may be particularly advantageous, for example, when the installation device 10 is utilized to deliver an implant 122 configured for lateral insertion, such as the implants shown and described, by way of example only, in the commonly owned and co-pending U.S. patent application Ser. No. 11/093,409, entitled "Systems and Methods for Spinal Fusion," and filed on Mar. 29, 2005; U.S. patent application Ser. No. 11/901,786, entitled "Systems and Methods for Spinal Fusion," and filed on Sep. 18, 2007; and U.S. Provisional Patent Application Ser. No. 61/032,945, entitled "Systems and Methods for Spinal Fusion and Deformity Correction," and filed on Feb. 29, 2008, the entire contents of each being incorporated herein by reference as if set forth fully herein. As previously mentioned, the distraction tangs 132 act as a guard when they are situated between the implant and the vertebral endplate. Closely matching the length of the distraction tangs 132 to the length of the selected implant may reduce the risk of endplate damage during implant delivery, while also ensuring that the distraction tangs 132 are not long enough to extend completely through the intervertebral disc space. It will be appreciated that distraction tangs 132 may be provided according to any range of lengths suitable to traverse a particular intervertebral space. According to one example, the distraction tangs 132 may be provided having lengths within a range including, but not necessarily limited to, 40 mm-60 mm. According to one example, a pair of distraction tans 132 may be provided for each of the lengths 40 mm, 50 mm, and 60 mm.

Any of a number of configurations may be utilized to detachably couple the distraction tangs 132 to the first and second arms 14, 16. As shown in the pictured embodiment, by way of example only, abutments 136 may include a grooves 138 extending laterally across the face of the abutments. As shown, the grooves 138 are a dovetail grooves. A complementary notch or ridge 140 situated on the proximal end of each distraction tang 132 may be slidably received within the grooves 138. Though not shown, it will be appreciated that a stop(s) may be provided on any of or any combination of the distraction tang 132 and the notch 140 to prevent the distraction tangs 132 from sliding all the way through grooves 138. According to one example, to temporarily fix the distraction tangs 132 to the arms 14, 16, the abutments 136 may be further provided with apertures 142 in open communication with the grooves 138. Setscrews 144 may be advanced through the apertures 142 such that they may engage the notches 140, locking the distraction tangs 132 in position.

It will also be appreciated that the non-parallel region 30 of the arms 14, 16 is longer than that of the device 110 to better accommodate the lateral approach. Rather than extending outward first and then converging together sharply to create space for the implant in the relatively short non-parallel region 30 of the installation device 10, the non-parallel region 30 of installation device 110 is extended and the arms 14, 16 converge towards each other directly. This creates a sleeker profile and allows the installation device to be advanced through smaller corridors (such as for example, retraction and/or distraction assemblies used to access the lateral aspect of the spine).

While specific embodiments have been shown by way of example in the drawings and described herein in detail, it will be appreciated that the invention is susceptible to various modifications and alternative forms. For example, although described primarily for use with a spinal fusion implant, the implant installation system 10 may be utilized to deliver other implants as well, such as for example, partial or total disc replacement implants, and corpectomy devices, among others. The description herein of specific embodiments is not intended to limit the invention to the particular forms disclosed, but on the contrary, the invention is to cover all modifications, equivalents, and alternatives falling within the spirit and scope of the invention.

What is claimed is:

1. A device for installing an implant between a first vertebra and a second vertebra having an intervertebral disc space therebetween, comprising:

a handle, a first arm and a second arm extending distally from the handle, a first distraction tang extending distally from the first arm, a second distraction tang extending distally from the second arm, and an inserter situated between the first and second arms and coupled to a translation member that moves the inserter along a portion of the first and second arms, the inserter configured to releasably couple to the implant, wherein the first distraction tang is configured to engage a first vertebral endplate when said device is positioned for delivering said implant and said second distraction tang is configured to engage a second vertebral endplate when said device is positioned for delivering said implant, wherein the first distraction tang and the second distraction tang are replaceable with distracting tangs of various lengths between 40 mm and 60 mm, said first and second arms comprising a proximal section adjacent the handle and a distal section, the first and second arms being configured to move relative to each other between a neutral position and an expanded position, wherein the first and second arms are parallel to each other in the proximal section and converge towards each other in the distal section when the first and second arms are in the neutral position, wherein movement of the inserter distally when said implant is coupled to said inserter causes said first and second arms to move towards the expanded position.

2. The device of claim 1, wherein the proximal section and the distal section are separated by an intermediate section.

3. The device of claim 2, wherein the first and second arms diverge away from one another in the intermediate section when the first and second arms are in the neutral position.

4. The device of claim 1, wherein the first distraction tang and the second distraction tang are replaceable with distraction tangs of various lengths.

5. The device of claim 4, wherein the first distraction tang and the second distraction tang each have a length of between 40 mm and 60 mm.

6. The device of claim 1, wherein a protrusion on the proximal end of the first distraction tang is received in a groove on the distal end the first arm to attach said first distraction tang to said first arm.

7. The device of claim 6, wherein an aperture in open communication with said groove is configured to receive a set screw therein to lock said first distraction tang to said first arm.

8. The device of claim 1, wherein at least a portion of an inner surface of the first and the second arms are smooth.

9. The device of claim 1, wherein a portion of the outer surface of at least one of the first distraction tang and the second distraction tang includes at least one surface feature.

10. The device of claim 9, wherein the at least one surface feature includes one or more of grooves and ridges.

11. The device of claim 1, wherein the inserter includes a pair of protrusions extending vertically to a height beyond said first arm and capturing the first arm therebetween.

12. The device of claim 1, wherein the inserter includes at least one abutment region extending vertically from one of said first arm and said second arm and configured to engage a surface of the vertebral body when said implant is advanced into said disc space.

13. The device of claim 1, wherein distraction tangs are provided having lengths of 40 mm, 50 mm, and 60 mm.

14. A device for installing an implant between a first vertebra and a second vertebra having an intervertebral disc space therebetween, the implant being installed from a lateral approach to the spine, comprising:

a handle, a first arm and a second arm extending distally from the handle, a first distraction tang extending distally from the first arm, a second distraction tang extending distally from the second arm, and an inserter situated between the first and second arms and coupled to a translation member that moves the inserter along a portion of the first and second arms, the inserter configured to releasably couple to the implant, wherein, the first distraction tang is configured to engage a first vertebral endplate when said device is positioned for delivering said implant and said second distraction tang is configured to engage a second vertebral endplate when said device is positioned for delivering said implant, the first distraction tang and the second distraction tang each having a length of between 40 mm and 60 mm, wherein movement of the inserter distally when said implant is coupled to said inserter causes said first and second arms to move away from each other and distract the disc space.

* * * * *